United States Patent
Oliver

(10) Patent No.: US 6,217,328 B1
(45) Date of Patent: Apr. 17, 2001

(54) ORAL HYGIENE SYSTEM

(76) Inventor: William L. Oliver, 1515 Ravenaux Ct., Southlake, TX (US) 76092

( * ) Notice: Subject to any disclaimer, the term of this patent is extended or adjusted under 35 U.S.C. 154(b) by 0 days.

(21) Appl. No.: 09/499,408

(22) Filed: Feb. 7, 2000

(51) Int. Cl.[7] ................................................. A61C 17/00
(52) U.S. Cl. .................................. 433/80; 433/29; 433/77
(58) Field of Search .................................. 433/77, 78, 79, 433/80, 29

(56) References Cited

U.S. PATENT DOCUMENTS

| | | |
|---|---|---|
| D. 397,788 | 9/1998 | Olson et al. . |
| 3,636,633 * | 1/1972 | Fuller et al. . |
| 4,209,908 * | 7/1980 | Fleer ........................................ 433/78 |
| 4,619,612 * | 10/1986 | Weber et al. ........................... 433/80 |
| 4,648,838 * | 3/1987 | Schlachter .............................. 433/29 |
| 4,902,225 * | 2/1990 | Löhn ...................................... 433/80 |
| 5,013,240 * | 5/1991 | Bailey et al. ........................... 433/77 |
| 5,062,796 | 11/1991 | Rosenberg . |
| 5,183,035 | 2/1993 | Weir . |
| 5,211,558 * | 5/1993 | Bailey et al. ........................... 433/77 |
| 5,344,317 | 9/1994 | Pacher et al. . |
| 5,503,553 | 4/1996 | Hines . |
| 5,634,791 | 6/1997 | Matsuura et al. . |
| 5,655,905 * | 8/1997 | Jaimes et al. ........................... 433/77 |
| 5,658,148 * | 8/1997 | Neuberger et al. ..................... 433/29 |

* cited by examiner

*Primary Examiner*—Ralph A. Lewis
(74) *Attorney, Agent, or Firm*—Henderson & Sturm LLP

(57) ABSTRACT

An oral hygiene system comprising a hand-held instrument attached to a mobile cart by an accessory hose. The instrument has two main components: a pistol-grip hand-piece, and an individualized patient attachment. The pistol-grip hand-piece includes irrigation, suction and brush speed controls, as well as an adjustable swivel piece for changing the orientation of the attachment. Inside the hand-piece is a light source with fiberoptic tubing which channels light to the attachment, and a two speed electric motor which powers a rotary brush. The attachment itself is a relatively inexpensive component, one of which is assigned to each patient. It is cylindrical with a right angle curve at the distal end, to which is attached a disposable rotary brush. An orifice for the suction, and irrigation portal, and the fiberoptic lighting are also located at the distal end of the attachment. The proximal end of the attachment attaches to the hand-piece at the swivel piece and a disposable, clear, plastic shield attaches to the attachment mechanism to protect the hand-piece from splatters.

6 Claims, 3 Drawing Sheets

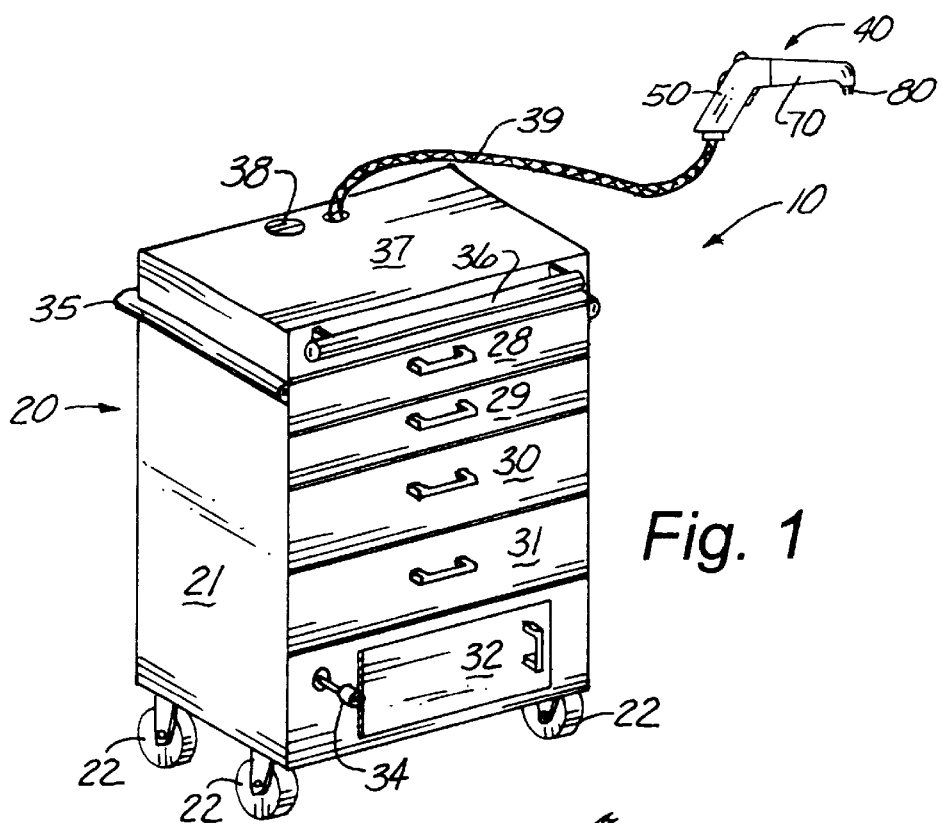
Fig. 1
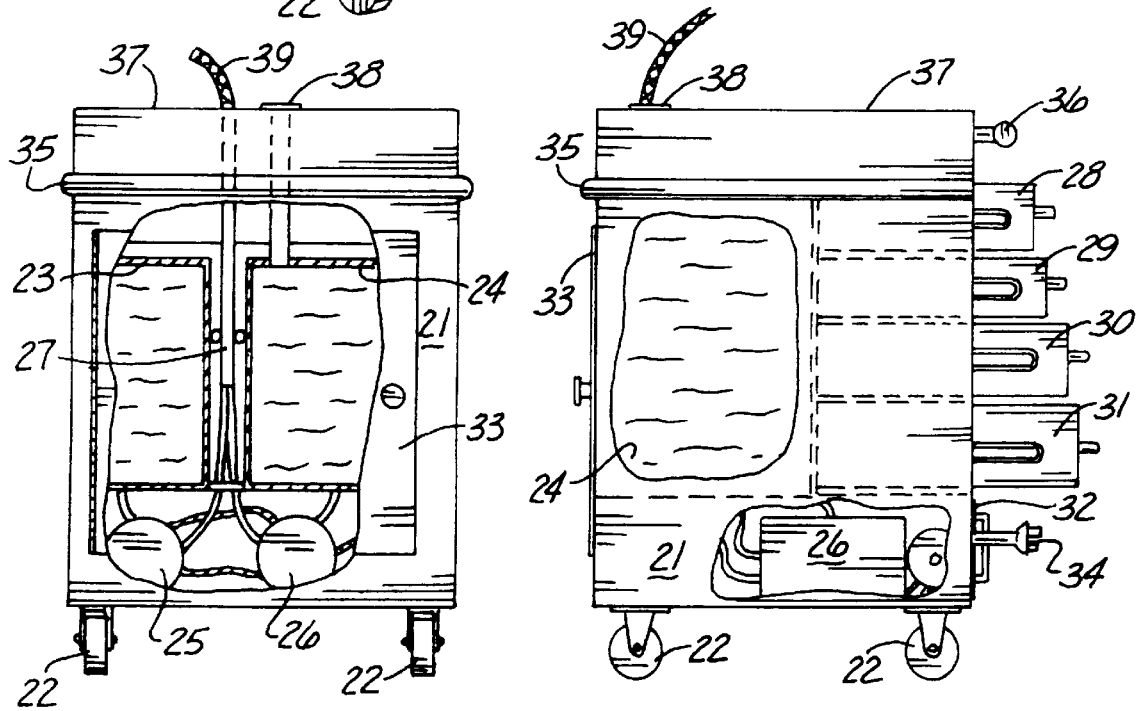
Fig. 2
Fig. 3

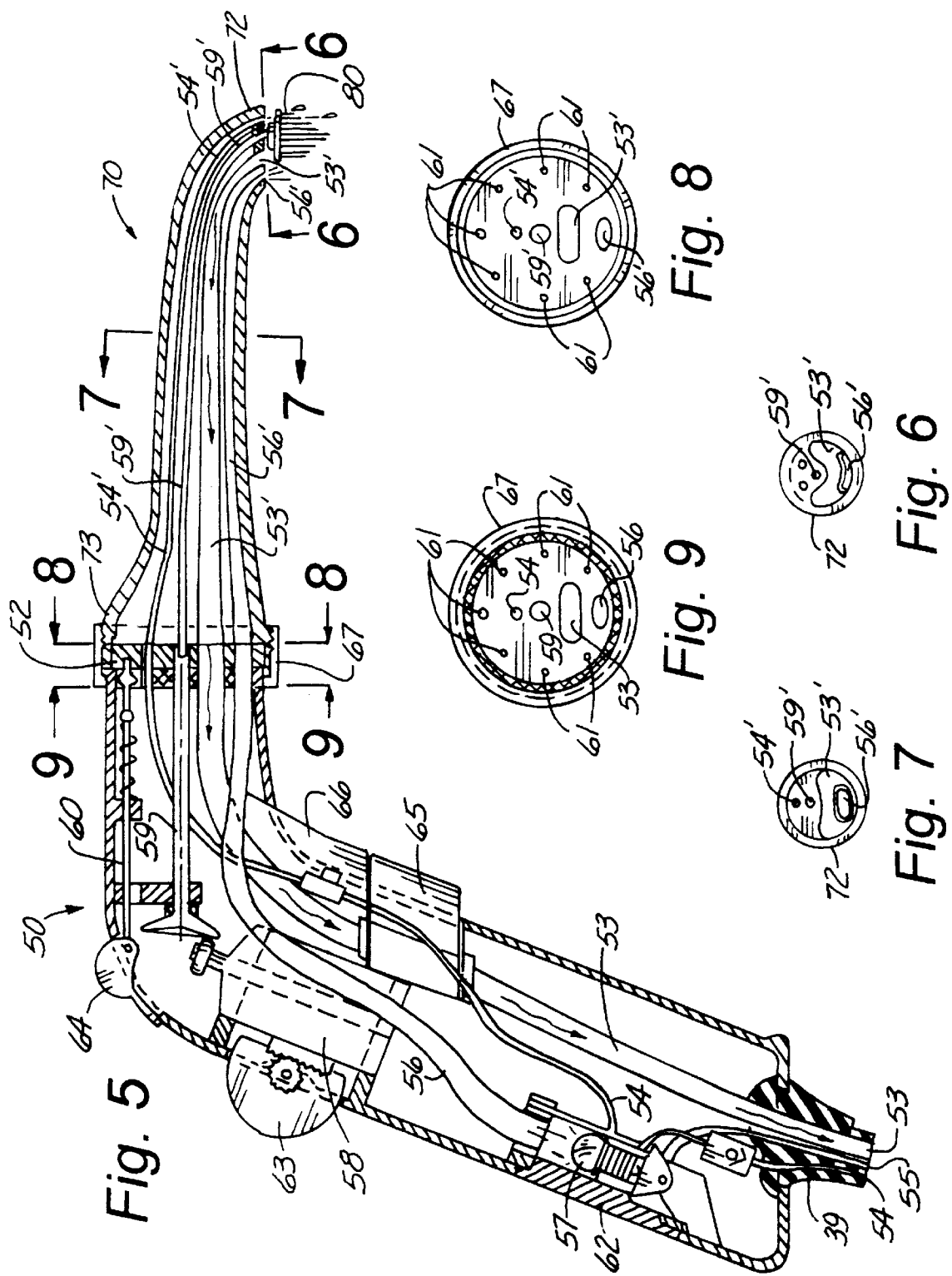

ORAL HYGIENE SYSTEM

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of oral hygiene systems, and more particularly to a system suitable to care for institutionalized individuals.

2. Description of Related Art

As can be seen by reference to the following U.S. Pat. Nos. D397,788; 5,062,796; 5,183,035; 5,344,317;5,503,553 and 5,634,791, the prior art is replete with myriad and diverse oral hygiene devices.

While all of the aforementioned prior art constructions are more than adequate for the basic purpose and function for which they have been specifically designed, they are uniformly deficient with respect to their failure to provide a simple, efficient, and practical oral hygiene system designed to provide adequate care to institutionalized individuals.

The methods used to provide oral hygiene to an institutionalized individual have remained essentially unchanged for many years and have proven to be inadequate even when administered conscientiously. This consists of a staff person using a conventional toothbrush and a dentifrice at the patient's bedside, or at a lavatory if the patient is not bedfast. Some commonly encountered problems using this method are: inadequate lighting for proper visualization of tooth surfaces; inadequate visualization due to accumulation of saliva, food debris, blood and toothpaste because the patient is unable to expectorate; the patient choking on salivary accumulations and/or toothpaste; the patient "pouching" food in the vestibule between the cheek and gums; inability to rinse a patient's mouth at the completion of the procedure; and staff non-compliance due to difficulty of the procedure.

As a consequence of the foregoing situation, there has existed a longstanding need for a new and improved oral hygiene system and the provision of such a construction is a stated objective of the present invention.

BRIEF SUMMARY OF THE INVENTION

Briefly stated, the present invention provides an oral hygiene system comprising a hand-held instrument attached to a mobile cart by an accessory hose. The instrument has two main components: a pistol-grip hand-piece, and an individualized patient attachment.

The pistol-grip hand-piece includes irrigation, suction and brush speed controls, as well as an adjustable swivel piece for changing the orientation of the attachment. Inside the hand-piece is a light source with fiberoptic tubing which channels light to the attachment, and a two speed electric motor which powers a rotary brush.

The attachment itself is a relatively inexpensive component, one of which is assigned to each patient. It is cylindrical with a right angle curve at the distal end, to which is attached a disposable rotary brush. An orifice for the suction, and irrigation portal, and the fiberoptic lighting are also located at the distal end of the attachment. The proximal end of the attachment attaches to the hand-piece at the swivel piece and a disposable, clear, plastic shield attaches to the attachment mechanism to protect the hand-piece from splatters.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the oral hygiene system of the present invention;

FIG. 2 is a rear elevational view of the mobile cart with portions cut away to reveal the interior components;

FIG. 3 is a side elevational view of the mobile cart with portions cut away;

FIG. 5 is a sectional view of the hand-piece and attachment showing the internal components;

FIG. 6 is a sectional view taken along line 6—6 of FIG. 5;

FIG. 7 is a sectional view taken along line 7—7 of FIG. 5;

FIG. 8 is a sectional view taken along line 8—8 of FIG. 5; and

FIG. 9 is a sectional view taken along line 9—9 of FIG. 5.

DETAILED DESCRIPTION OF THE INVENTION

Figure 4:
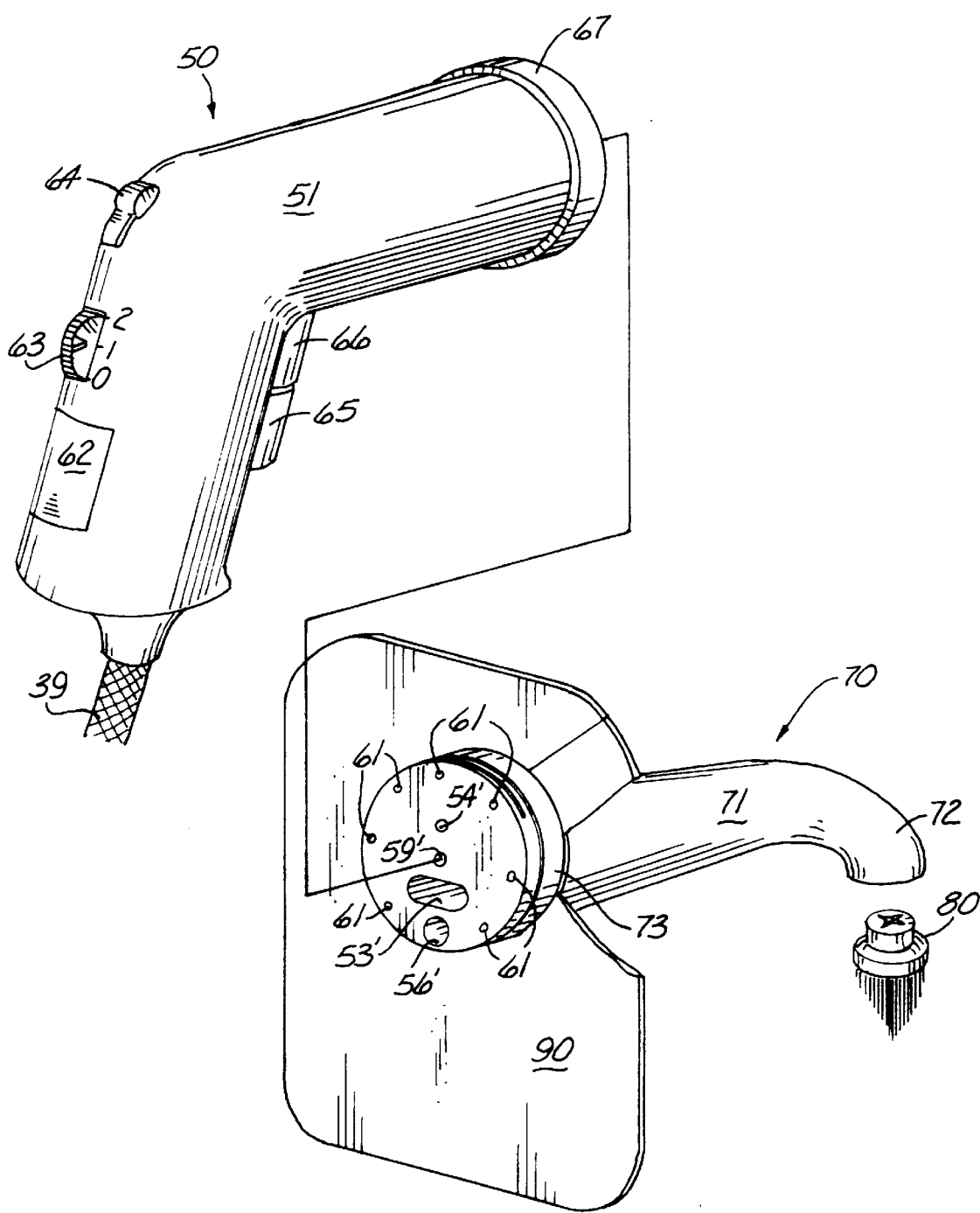
FIG. 4 is an exploded perspective view of the pistol-grip hand-piece and the individualized patient attachment.

As can be seen by reference to the drawings, and in particularly to FIG. 1, the oral hygiene system that forms the basis of the present invention is designated generally by the reference number 10.

The system 10 includes a mobile cart 20 and a handheld instrument 40. As best shown in FIGS. 1–3, the cart 20 comprises a housing 21 supported by caster wheels 22. The housing 21 encloses reservoirs 23, 24 for suction waste and irrigation fluids, a vacuum pump 25, a fluid pump 26, a hose retraction device 27, and storage drawers 28, 29, 30 and 31. Front and rear doors 32, 33 provide access to the interior components, and a retractable electrical plug 34 extends through a front wall. A protective bumper 35 extends around the upper portion of the housing 21 and a handrail 35 is carried on the front thereof. The top work area 37 has a port 38 for refilling the irrigation fluid and an opening for a retractable hose 39.

As most clearly shown in FIGS. 4 and 5, the handheld instrument 40 includes a pistol-grip hand-piece 50 and an individualized patient attachment 70. The hand-piece 50 includes a housing 51 formed in the shape of a pistol grip having a proximal end that receives the retractable hose 39 and a distal end that carries an adjustable swivel piece 52. A vacuum line 53, an irrigation fluid line 54, and a power line 55 are fed into the hand-piece 50 by the hose 39. A fiberoptic bundle 56 extends from a water cooled light source 57 to the distal end of the hand-piece 50. A two-speed electric motor 58 drives a rotary shaft 59 which extends into the swivel piece 52. A spring biased retractable locking pin 60 also extends into the swivel piece 52 where it selectively engages one of a number of pin holes 61 (FIGS. 8 and 9). The exterior of the housing 51 carries a light source access panel 62, a brush speed control switch 63, a retractable pin actuator 64, a trigger vacuum control 65, and a trigger irrigation fluid control 66.

A retaining collar 67 selectively connects the hand-piece 50 to a selected one of a number of individualized patient attachments 70. Each attachment 70 includes a housing 71 and a curved distal end 72 to which a rotary brush 80 is attached. A disposable clear plastic shield 90 connects to the proximal end 73 to protect the hand-piece 50 from splatters. The interior of the housing 71 carries a complementary vacuum line 53', irrigation fluid line 54', fiberoptic bundle 56', and drive shaft 59' that register and are coupled with the vacuum line 53, irrigation line 54, fiberoptic bundle 56, and drive shaft 59 of the hand-piece 50.

The mobile cart 20 houses a vacuum pump 25, an irrigation pump 26, and reservoirs for suction waste 23 and irrigation fluid 24. Irrigation fluid such as antiseptic or water is pumped from the cart reservoir 24 through the hose 39, hand-piece 50 and attachment 70 to the mouth where it functions with the rotary brush 80 to loosen debris from the teeth. Fluids and debris are in turn picked up by the suction 53'at the distal end 71 of the attachment 70 and are taken to the waste reservoir 23 in the cart 20. The waste reservoir 23 is emptied when full. The cart 20 has drawers 28, 29, 30 and 31 with compartments for storing each attachment 70 in an antiseptic solution. Other storage space is present for miscellaneous items such as replacement brushes, bibs, denture adhesives, mouthwashes, cups and toothpaste. An ultrasonic cleaner may be located on top of the cart 20 for denture cleaning, as well as a retractable saliva ejector to the used as an adjunct to the suction in the attachment 70. A rechargeable 12V battery powers the unit. A retractable 110V plug 34 supplies power to recharge the battery and may be used to power the unit when the battery is charging.

The oral hygiene system 10 is designed to provide a simplified and thorough method of removing plaque, food debris and salivary accumulations from the teeth and oral cavity of an institutionalized individual. It is intended to be operated on a routine basis after meals by a trained staff operator, for those persons incapable of providing adequate oral hygiene for themselves. The instrument 40 is designed to be operated by one hand, leaving the other hand free to retract the lips and tongue, manipulate the saliva ejector, or use a mouth prop. The instrument 40 provides mechanical removal of plaque and food debris, irrigation, fiberoptic lighting and suction. The purpose of system 10 is to prevent oral disease in institutionalized individuals.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. An oral hygiene system, comprising:

a mobile cart;

an irrigation fluid reservoir mounted on the cart:

an irrigation fluid pump mounted on the cart and disposed in fluid communication with the irrigation fluid reservoir;

a waste fluid reservoir mounted on the cart;

a vacuum pump mounted on the cart and disposed in fluid communication with the waste fluid reservoir;

a handheld instrument including an irrigation port attached in fluid communication with the irrigation fluid reservoir and an adjacent suction port attached in fluid communication with the waste fluid reservoir;

a fiberoptic light source disposed within the handheld instrument and having a emitting end disposed adjacent the irrigation port and the suction port; and a motor and operably attached drive shaft disposed within the handheld instrument and having a shaft end disposed adjacent the irrigation port, the suction port, and the light emitting end wherein the handheld instrument includes a pistol-grip shaped hand-piece and an individualized patient attachment which includes a right-angled curved end which carries the irrigation port, the suction port, the light emitting end, and the shaft end.

2. The system of claim 1 wherein the handheld instrument is operably attached to the mobile cart by a hose.

3. The system of claim 2 wherein the hose is retractable within the mobile cart.

4. The system of claim 1 wherein the shaft end is disposed to selectively receive a disposable brush.

5. The system of claim 4 wherein the attachment is disposed to carry a splash shield.

6. The system of claim 5 wherein the mobile cart includes a plurality of supply storage drawers.

* * * * *